United States Patent
Kim et al.

(10) Patent No.: US 11,185,488 B2
(45) Date of Patent: Nov. 30, 2021

(54) SKIN EXTERNAL PREPARATION COMPOSITION FOR MOISTURIZING SKIN CONTAINING 1,2,3,4,6-PENTA-O-GALLOYL-β-D-GLUCOSE

(71) Applicant: AMOREPACIFIC CORPORATION, Seoul (KR)

(72) Inventors: Kyu Han Kim, Yongin-si (KR); Eui Dong Son, Yongin-si (KR); Jin Sup Shim, Yongin-si (KR); Tae Ryong Lee, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 16/650,575

(22) PCT Filed: Jul. 31, 2018

(86) PCT No.: PCT/KR2018/008693
§ 371 (c)(1),
(2) Date: Mar. 25, 2020

(87) PCT Pub. No.: WO2019/066237
PCT Pub. Date: Apr. 4, 2019

(65) Prior Publication Data
US 2020/0230044 A1    Jul. 23, 2020

(30) Foreign Application Priority Data
Sep. 26, 2017   (KR) .......................... 10-2017-0123915

(51) Int. Cl.
*A61K 8/60* (2006.01)
*A61K 8/92* (2006.01)
*A61Q 19/00* (2006.01)

(52) U.S. Cl.
CPC .............. *A61K 8/602* (2013.01); *A61K 8/922* (2013.01); *A61Q 19/007* (2013.01)

(58) Field of Classification Search
CPC ....... A61K 8/602; A61K 8/922; A61Q 19/007
See application file for complete search history.

(56) References Cited

U.S. PATENT DOCUMENTS

| | | | |
|---|---|---|---|
| 9,877,915 B2 | 1/2018 | Choi et al. | |
| 2007/0196296 A1* | 8/2007 | Osborne | A61K 8/602 424/61 |
| 2009/0170788 A1* | 7/2009 | Shin | A61P 17/00 514/27 |
| 2017/0112737 A1 | 4/2017 | Bernard et al. | |

FOREIGN PATENT DOCUMENTS

| | | |
|---|---|---|
| JP | 2011-006341 A | 1/2011 |
| KR | 10-2016-0127137 A | 11/2016 |
| KR | 10-1709734 B1 | 2/2017 |
| WO | 2017/122495 A1 | 7/2017 |

OTHER PUBLICATIONS

Ruxi Wang, et al., "Wound-healing plants from TCM: in vitro investigations on selected TCM plants and their influence on human dermal fibroblasts and keratinocytes", Fitoterapia, 2013, pp. 308-317, vol. 84.
Fernanda Giacomini Bueno, et al., "Hydrolyzable tannins from hydroalcoholic extract from Poincianella pluviosa stem bark and its wound-healing properties: Phytochemical investigations and influence on in vitro cell physiology of human keratinocytes and dermal fibroblasts", Fitoterapia, 2014, pp. 252-260, vol. 99.
International Search Report for PCT/KR2018/008693 dated Nov. 5, 2018 (PCT/ISA/210).

* cited by examiner

*Primary Examiner* — Pancham Bakshi
(74) *Attorney, Agent, or Firm* — Sughrue Mion, PLLC

(57) ABSTRACT

A skin external composition containing 1,2,3,4,6-penta-O-galloyl-β-D-glucose (hereinafter referred to as "PGG") and its use to improve moisture balance of skin are disclosed. The skin external composition, due to containing PGG, stimulates the formation of filaggrin in keratinocytes, increases loricrin and involucrin expression, thereby stimulating the formation of a normal keratin layer, and as a result, can strengthen the skin barrier function to provide an excellent skin moisturization improving effect. Thus, the composition is effective in improving moisture balance of skin. A method for moisturizing the skin using the composition is also disclosed.

3 Claims, 3 Drawing Sheets

[FIG. 1]
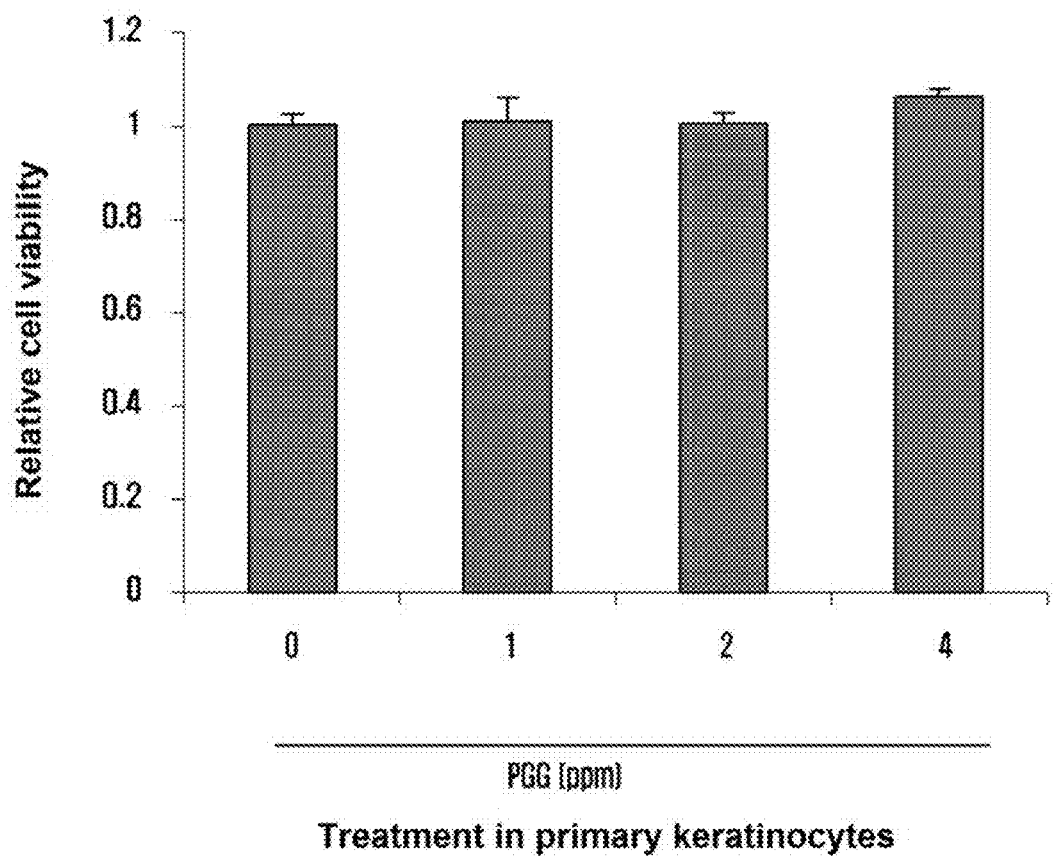

[FIG. 2]
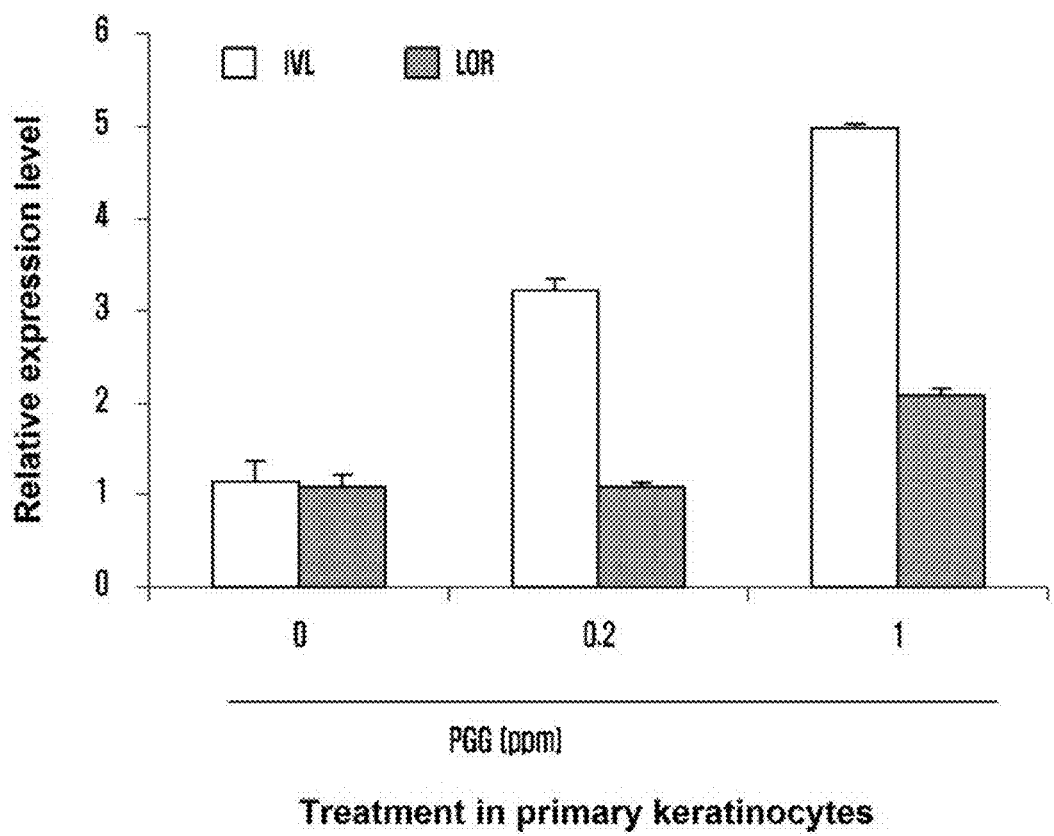

[FIG. 3]
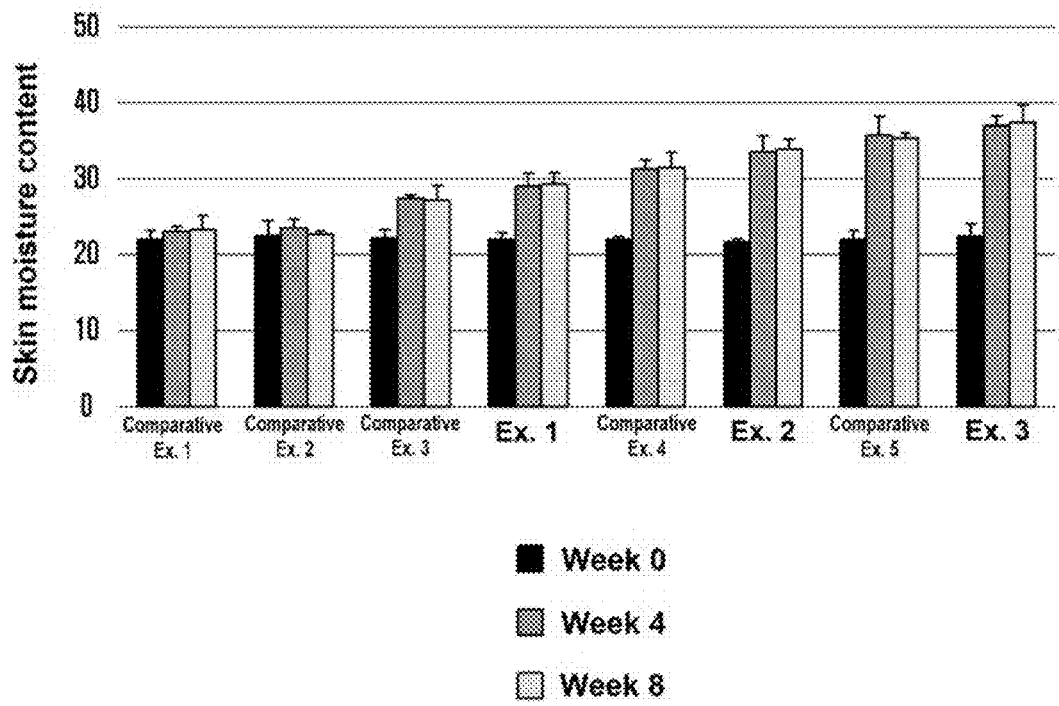
[FIG. 4]
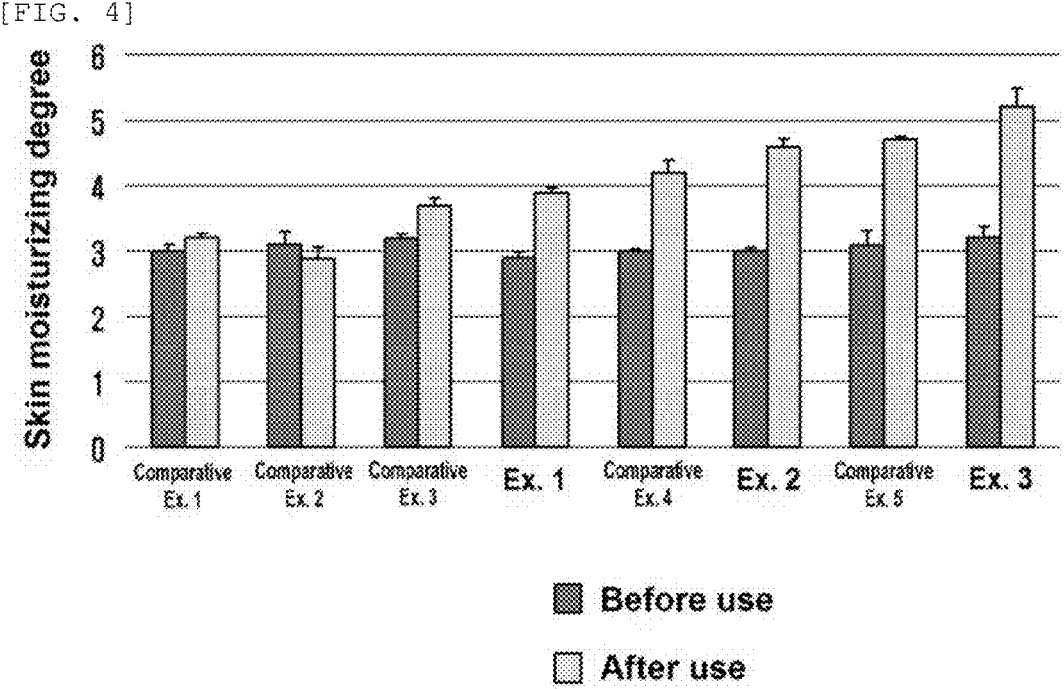

SKIN EXTERNAL PREPARATION COMPOSITION FOR MOISTURIZING SKIN CONTAINING 1,2,3,4,6-PENTA-O-GALLOYL-β-D-GLUCOSE

CROSS REFERENCE TO RELATED APPLICATIONS

This application is a National Stage of International Application No. PCT/KR2018/008693 filed Jul. 31, 2018, claiming priority based on Korean Patent Application No. 10-2017-0123915 filed Sep. 26, 2017.

TECHNICAL FIELD

The present disclosure relates to a skin external preparation composition containing 1,2,3,4,6-penta-O-galloyl-β-D-glucose (hereinafter referred to as "PGG"), and more particularly, to a skin external preparation composition, a use thereof, and a method for moisturizing the skin using the same, wherein the skin external preparation composition, due to containing PGG, stimulates the formation of filaggrin in keratinocytes, increases the expression of loricrin and involucrin, thereby stimulating the formation of a normal keratin layer, and as a result, can strengthen the skin barrier function to provide an excellent skin moisturizing improving effect.

BACKGROUND ART

The main function of keratin layer is to protect the skin by preventing the evaporation of moisture from the skin or by preventing the penetration of harmful substances from the outside. In particular, 30% of water is present in the keratin layer on dry weight basis, of which 20% is present in corneocytes and 10% is present in intercellular lipids. Water in corneocytes is present in combination with natural moisturizing factors (NMFs) from which filaggrin is degraded.

Filaggrin is expressed in association with terminal differentiation in the course of epidermal differentiation process, and involucrin and loricrin, in addition to filaggrin, are also important markers related to moisturizing. Loricrin is a protein expressed during terminal differentiation, which is required for keratinocytes to differentiate and form stable keratin, and is a substance that accounts for 70 to 85% of the keratin mass. However, it has a domain rich in glutamine and lysine that can participate in cross-linking between transglutaminase-catalyzed peptides, and it conducts an important role in keratin formation by helping cross-linking between keratin-forming proteins. Since such loricrin binds to the cell membrane in the upper granular layer and is completed as a protein, it is used as a marker in tracking the terminal differentiation process of keratinocytes.

An increase in markers such as filaggrin, involucrin, and loricrin means that intracellular lipids, which are the precursors of NMF in corneocytes, were normalized through the formation of a normal keratin layer. Therefore, in order to form a keratin layer so as to strengthen the skin barrier that prevents the loss of moisture in the skin tissue, while promoting the maintenance of moisture in skin tissues so as to prevent skin aging and to maintain skin health from external environmental changes such as air drying, ultraviolet rays and various pollutants, there is a need to develop a skin moisturizing substance that promotes the expression of markers such as filaggrin, involucrin, and loricrin.

PRIOR ART CITATION (Patent Document 1) Korean Patent Registration No. 10-1709734 (Publication date: Feb. 23, 2017)

DETAILED DESCRIPTION OF THE INVENTION

Technical Problem

Accordingly, the present inventors confirmed that after screening for substances that increase the gene expression of filaggrin by treating various substances reported as indicators of various natural products such as soybean, green tea, and ginseng to epidermal cells, the moisturizing marker increases through the expression of loricrin, involucrin and the like, and also confirmed that 1,2,3,4,6-penta-O-galloyl-β-D-glucose showed a result of increasing the expression of loricrin and involucrin, as well as the gene expression of filaggrin. In addition, the inventors confirmed that when 1,2,3,4,6-penta-O-galloyl-β-D-glucose is used together with a hardened vegetable oil, these effects are much more improved, thereby completing the present disclosure.

Therefore, an object of the present invention is to provide a skin external preparation composition which, due to containing 1,2,3,4,6-penta-O-galloyl-β-D-glucose and a hardened vegetable oil, stimulates the formation of a normal keratin layer, thereby improving a skin moisturizing capacity, a use thereof, and a method for moisturizing skin using the same.

Technical Solution

In order to achieve that above objects, the present disclosure provides an external preparation composition for moisturizing skin including 1,2,3,4,6-penta-O-galloyl-β-D-glucose and a hardened vegetable oil as active ingredients, a use thereof, and a method for moisturizing the skin using the same. More specifically, the present disclosure provides a use of a mixture of 1,2,3,4,6-penta-O-galloyl-β-D-glucose and a hardened vegetable oil in the preparation of a skin external preparation for moisturizing the skin. In addition, the present invention a method for moisturizing the skin using the skin external preparation composition including 1,2,3,4,6-penta-O-galloyl-β-D-glucose and a hardened vegetable oil as active ingredients

Advantageous Effects

The composition of the present disclosure includes 1,2,3,4,6-penta-O-galloyl-β-D-glucose and a hydrogenated vegetable oil to promote the formation of a normal keratin layer, thereby enhancing the barrier function of the skin and finally providing an excellent effect of improving the moisturizing power of the skin.

BRIEF DESCRIPTION OF THE DRAWINGS

FIG. 1 shows the results of confirming the viability of cell by treating PGG according to concentration.

FIG. 2 shows the results of measuring the gene expression levels of involucrin (IVL) and loricrin (LOR) by PGG by treating keratinocytes with 0.2 ppm or 1 ppm of PGG and then separating mRNA.

FIG. 3 shows the degree of increase in skin moisture content of a PGG-containing formulation.

FIG. 4 shows the results of a sensory evaluation for the skin moisturizing degree of the PGG-containing formulation.

DETAILED DESCRIPTION OF THE EMBODIMENTS

The skin external preparation composition of the present disclosure includes 1,2,3,4,6-penta-O-galloyl-β-D-glucose and a hardened vegetable oil as active ingredients.

1,2,3,4,6-Penta-O-galloyl-β-D-glucose (PGG) is a tannin acting on an organism, and is present in many medicinal plants and is known to have various biological activities such as anti-inflammatory, anti-oxidant, anti-cancer, and anti-viral effects (see B. M. Choi, et al., Neurosci. Lett, 328:185-189, 2002; L. L. Ho, et al., Eur. J. Pharmacol., 453:149-158, 2002; D. G. Rang, et al., Eur. J. Pharmacol., 524:111-119, 2005; S. J. Lee, et al., Biol. Pharm. Bull., 29:2131-2134, 2006). It is a compound having the structure of the following Chemical Formula 1, which is present in various plants such as peonies root, aboveground parts including leaves of turmeric, and *Juglans mandshurica*.

[Chemical Formula 1]

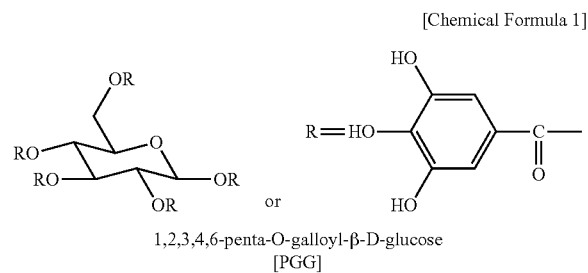

1,2,3,4,6-penta-O-galloyl-β-D-glucose
[PGG]

The PGG used herein may be directly extracted and used from various plants by a method known in the art, or commercially available products can be purchased and used.

The hardened vegetable oil used herein is at least one selected from the group consisting of hardened palm oil, hardened rapeseed oil, hardened canola oil, hardened olive oil, and mixtures thereof.

The skin external preparation composition according to the present disclosure may contain PGG in an amount of 0.01 to 1.0% by weight, preferably 0.05 to 0.2% by weight based on the total weight of the composition. When the content of PGG less than 0.01% by weight, a sufficient skin moisturizing effect cannot be obtained, and when the content exceeds 1.0% by weight, a safety and a formulation stability may be lowered.

In addition, the skin external preparation composition according to the present disclosure may contain a hardened vegetable oil in an amount of 0.001 to 2.0% by weight, preferably 1.2 to 1.7% by weight based on the total weight of the composition. When the hardened vegetable oil is included in the above range, not only it is suitable to exhibit the intended effect of the present disclosure, but also it can satisfy both the stability of the composition and the stability of the formulation, and from the viewpoint of cost-effectiveness, it may be appropriate to include in the above range. Specifically, when the amount of the mixture of PGG and a hydrogenated vegetable oil is less than 0.011% by weight, a sufficient skin moisturizing effect cannot be obtained, and if the amount exceeds 3.0% by weight, a safety and a formulation stability may be lowered.

The composition of the present disclosure can be used as a moisturizing skin external preparation composition, which enhances not only the gene expression of filaggrin, but also the expression of loricrin and involucrin, thereby inducing the differentiation of skin corneocytes, promoting the formation of normal keratin layer and enhancing skin barrier function. Therefore, it can be usefully used as a skin external preparation composition for preventing or improving skin dryness, atopic dermatitis, contact dermatitis, psoriasis or the like caused by incomplete epidermal differentiation.

The composition according to the present disclosure can be formulated as a cosmetic composition or a pharmaceutical composition, but is not limited thereto.

The composition according to the present disclosure may be formulated by containing cosmetic dermatologically acceptable media or bases. This is all formulations suitable for topical application, and for example, it can be provided in the form of solutions, gels, solids, kneaded anhydrous products, or in the form of emulsions obtained by dispersing an oil phase in an aqueous phase, suspensions, microemulsions, microcapsules, micro-granulocyte or ionic (liposomal) and nonionic vesicle dispersants, or in the form of cream, skin lotion, powder, ointment, spray or conceal stick. It can also be used in the form of a foam or in the form of an aerosol composition further containing a compressed propellant. These compositions can be prepared according to conventional methods in the art.

Further, the composition according to the present disclosure may contain adjuvants commonly used in the cosmetic or dermatological fields, such as a fatty substance, an organic solvent, a solubilizer, a thickener, a gelling agent, a softener, an antioxidant, a suspending agent, a stabilizer, a foaming agent, a fragrance, a surfactant, water, an ionic or nonionic emulsifier, a filler, a sequestering agent, a chelating agent, a preservative, vitamin, a blocker, a wetting agent, an essential oil, a dye, a pigment, a hydrophilic or lipophilic activator, a lipid vesicle or any other ingredients commonly used in cosmetics. The adjuvant is introduced in an amount commonly used in the cosmetic or dermatological field.

Further, the composition of the present disclosure may contain a substance that promotes skin absorption in order to increase the effect of improving skin moisturization.

In another embodiment of the present disclosure, there can be provided use of the skin external preparation composition according to the present disclosure for improving skin moisturizing effect. Specifically, according to the present disclosure, in the preparation of an external preparation composition for moisturizing skin, preferably a cosmetic composition, a mixture of 1,2,3,4,6-penta-O-galloyl-β-D-glucose and hardened vegetable oil can used as effective moisturizing ingredients.

In yet another embodiment of the present disclosure, there can be provided a method for maintaining or improving moisturizing power for skin including topically applying the skin external preparation composition containing the mixture of 1,2,3,4,6-penta-O-galloyl-β-D-glucose of the present disclosure and a hardened vegetable oil as effective moisturizing ingredients to a subject in need of skin moisturizing.

Hereinafter, the configuration and effects of the present disclosure will be described in more detail with reference to test examples and formulation examples. However, these test examples and formulation examples are provided illustrative purposes only to aid understanding of the present invention, and the scope of the present disclosure is not limited by the following examples.

[Reference Example 1] Preparation of PGG

The PGG used below was obtained from SIGMA-ALDRICH.

[Reference Example 2] Preparation of Hardened Vegetable Oil

In the following, Akogel Plus obtained from Aston Chemicals was used as the hydrogenated vegetable oil.

[Test Example 1] Evaluation of Cytotoxicity of PGG

Neonatal keratinocytes (obtained from Lonza) was dispensed into a 60 mm cell culture dish at a density of $1.25 \times 10^6$ cells/dish using KGM medium, and then cultured at 37° C. in a 5% $CO_2$ incubator up to about 80% confluency. Then, the cells were treated with PGG at concentrations of 0 ppm, 1 ppm, 2 ppm, and 4 ppm, cultured for 4 days, and then the viability of the cells was confirmed. The result of the confirmation is shown in FIG. 1.

Referring to FIG. 1, it can be confirmed that there is no significant difference in cell viability depending on the difference in concentration of PGG, and that PGG is a substance having no cytotoxicity.

[Test Example 2] Measurement of the Gene Expression Level of Filaggrin (RNA Separation and RT-PCR)

Neonatal keratinocytes (obtained from Lonza) was dispensed into a 60 mm cell culture dish at a density of $1.25 \times 10^6$ cells/dish using KGM medium, and then cultured at 37° C. in a 5% $CO_2$ incubator up to about 80% confluency. Then, eight compounds including PGG from soybean, green tea, ginseng, and other natural products were selected as test substances (Table 1), and the cells were treated with each of these compounds at 1 ppm and cultured for 2 days. After the culture, the medium was removed, and 1 ml of Trizol (Invitrogen) was added, and mRNA was isolated according to an RNA isolation method of Invitrogen. mRNA was quantified at 260 nm using an ultraviolet detector (Hewlett Packard), and RT-PCR (Reverse Transcription-Polymerase Chain Reaction) was performed. For genetic analysis of each sample, correction was performed based on the complementary gene, RPL13A, and the expression level of filaggrin for each sample is shown in Table 1 below.

TABLE 1

The rate of increase in filaggrin expression by test substances obtained from natural products

| Compound | Increase in filaggrin expression(%) |
|---|---|
| Vehicle (Control) | — |
| 6,7,4'-trihydroxyisoflavone | 103 |
| 7,3',4'-trihydroxyisoflavone | 110 |
| Syringaresinol | 103 |
| Astragalin | 105 |
| (−)-Epicatechin(EC) | 108 |
| Paeoniflorin | 116 |
| Albiflorin | 107 |
| PGG | 229 |

Looking at the results shown in Table 1 above, it can be confirmed that in the case of the sample treated with other compounds, the rate of increase in the expression of filaggrin was not large, but in the case of the sample treated with PGG, it exhibited a rate of increase in the expression of filaggrin by more than 2 times that of the control group.

[Test Example 3] Gene Increase Experiment for Involucrin (IVL) and Loricrin (LOR) (RNA Isolation and RT-PCR)

Neonatal keratinocytes was dispensed into a 60 mm cell culture dish at a density of $1.25 \times 10^6$ cells/dish using KGM medium, and then cultured at 37° C. in a 5% $CO_2$ incubator up to about 80% confluency. Then, the keratinocytes were treated with 0.2 ppm or 1 ppm of PGG, cultured for 4 days. After the culture, the medium was removed and 1 ml of Trizol (Invitrogen) was added thereto, and mRNA was isolated according to the RNA isolation method of Invitrogen. After quantifying mRNA at 260 nm using a CV detector (HEWLETT PACKARD), RT-PCR (Reverse transcription-polymerase chain reaction) was performed by using the primers of LOR and IVL (LOR-HS01894962_s1, IVL HS00846307_s1, respectively, both of which were obtained from Life Technologies). For genetic analysis of each sample, the correction was performed based on the complementary gene, RPLP0, and the results are shown in Table 2 below.

Referring to FIG. 2, it can be seen that when the PGG was treated at a concentration of 0.2 ppm, the expression level of loricrin gene had almost no difference compared to the control group, but the involucrin gene exhibited a three-fold or more increase is the expression level compared to the control group.

In addition, when the PGG was treated at a concentration of 1 ppm, it can be confirmed that the involucrin gene was increased 5 times and the loricrin gene increased 2 times or more compared to the control group.

[Reference Example 3] Preparation Examples and Comparative Examples

In accordance with the composition shown in Table 2 below, a softening lotion was produced by an ordinary method (unit: % by weight).

TABLE 2

| Ingredients | Comparative Example 1 | Comparative Example 2 | Comparative Example 3 | Comparative Example 4 | Comparative Example 5 | Example 1 | Example 2 | Example 3 |
|---|---|---|---|---|---|---|---|---|
| Purified water | Residual amount | Residual amount | Residual amount | Residual amount | Residual amount | Residual amount | Residual amount | Residual amount |
| PGG(0.1%) | — | — | 0.05 | 0.1 | 0.2 | 0.05 | 0.1 | 0.2 |
| Hardened vegetable oil | — | 1.5 | — | — | — | 1.5 | 1.5 | 1.5 |
| Stearic acid | 0.6 | 0.6 | 0.6 | 0.6 | 0.6 | 0.6 | 0.6 | 0.6 |
| Glycerol stearate | 1 | 1 | 1 | 1 | 1 | 1 | 1 | 1 |
| Stearyl alcohol | 2.5 | 2.5 | 2.5 | 2.5 | 2.5 | 2.5 | 2.5 | 2.5 |
| Behenyl alcohol polyglycerol-10 pentastearate & sodium stearoyl lactylate | 1 | 1 | 1 | 1 | 1 | 1 | 1 | 1 |
| Arachidyl behenyl alcohol & arachidylglucoside | 1 | 1 | 1 | 1 | 1 | 1 | 1 | 1 |
| Cetylaryl alcohol & cetaryl glucoside | 2 | 2 | 2 | 2 | 2 | 2 | 2 | 2 |
| PEG-100 stearate, glycerol oleate & propylene glycol | 1.5 | 1.5 | 1.5 | 1.5 | 1.5 | 1.5 | 1.5 | 1.5 |
| Caprylic/capric triglyceride | 11 | 11 | 11 | 11 | 11 | 11 | 11 | 11 |
| Cyclomethicone | 6 | 6 | 6 | 6 | 6 | 6 | 6 | 6 |
| Preservatives, fragnance | Proper amount | Proper amount | Proper amount | Proper amount | Proper amount | Proper amount | Proper amount | Proper amount |
| Triethanol amine | 0.1 | 0.1 | 0.1 | 0.1 | 0.1 | 0.1 | 0.1 | 0.1 |

[Test Example 4] Evaluation of Skin Water Content and Skin Moistness

In order to examine the skin moisturizing power of Comparative Examples 1 to 5 and Examples 1 to 3 of Reference Example 3, evaluation was made as follows.

80 women in their 30s and 40s were divided into 8 groups of 10 women each, and the softening lotions of Comparative Examples 1 to 5 or Examples 1 to 3 were applied to the face twice a day every morning and evening for 8 weeks.

Before the start of application, and when 4 weeks and 8 weeks passed after the application, the moisture content of the skin was measured using skin moisture meter (Corneometer CM825 is C+K Electronic Co., Germany) under constant temperature and constant humidity conditions (24° C., relative humidity 40%). The result is shown in FIG. 3. The result value in FIG. 3 means the moisture content of the skin.

Referring to FIG. 3, it can be seen that in the case of Comparative Example 1 not containing both EGG and a hardened vegetable oil, and Comparative Example 2 containing only a hardened vegetable oil, the skin moisture content hardly increased, but in the case of Comparative Examples 3 to 5 containing EGG alone, the skin moisture content increased in a concentration-dependent manner at 4 and 8 weeks compared to Comparative Example 1.

In addition, it can be confirmed that in Examples 1 to 3 containing PGG and a hardened vegetable oil together, the skin moisture content was further increased compared to Comparative Examples 3 to 5.

Further, for the sensory evaluation, the skin moisturizing degree before and after use from users using the softening agents of Comparative Examples 1 to 5 or Examples 1 to 3 (4 weeks after application) was scored from 1 to 5 points (1 point: very bad, 5 points: very good), and the results are shown in FIG. 4.

Looking at FIG. 4, it can be confirmed that in the case of Comparative Example 1 not containing both PGG and a hardened vegetable oil, and Comparative Example 2 containing only a hardened vegetable oil, the degree of moistening of the skin hardly changed, but in the case of Comparative Examples 3 to 5 containing PGG alone, skin moisturization increased on the fourth week after application compared to Comparative Example 1, and further, in the case of Examples 1 to 3 containing both EGG and a hardened vegetable oil, the skin moistness was further increased compared to Comparative Examples 3 to 5.

The invention claimed is:

1. A method for improving moisture balance of skin of a subject, comprising applying a cosmetic composition to the skin, wherein the cosmetic composition contains 1,2,3,4,6-penta-O-galloyl-β-D-glucose (PGG) of the following Chemical Formula 1 and a hydrogenated vegetable oil as active ingredients:

Chemical Formula 1

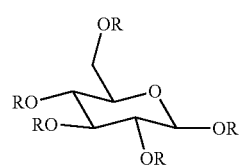

wherein
all of Rs are

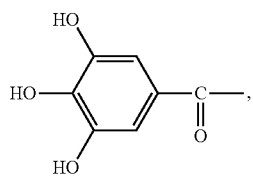

wherein the hydrogenated vegetable oil is one or more selected from the group consisting of hydrogenated palm oil, hydrogenated rapeseed oil, hydrogenated canola oil, hydrogenated olive oil, and a mixture thereof, wherein the hydrogenated vegetable oil is contained in an amount of 1.2 to 1.7% by weight based on a total weight of the composition.

2. The method of claim 1, wherein the 1,2,3,4,6-penta-O-galloyl-β-D-glucose is contained in an amount of 0.01 to 1.0% by weight based on the total weight of the composition.

3. The method of claim 1, wherein the composition increases the gene expression of filaggrin.

* * * * *